United States Patent [19]

Citri

[11] Patent Number: 5,614,375
[45] Date of Patent: Mar. 25, 1997

[54] METHOD AND TEST KIT FOR THE RAPID DETECTION OF BIOTOXIC CONTAMINANTS

[75] Inventor: Nathan Citri, Jerusalem, Israel

[73] Assignee: Yissum Research Development Co. of the Hebrew University of Jerusalem, Israel

[21] Appl. No.: 217,168

[22] Filed: Mar. 23, 1994

[51] Int. Cl.$^6$ ............... C12Q 1/02; C12Q 1/32; C12M 3/00; C12M 1/20
[52] U.S. Cl. ............... 435/29; 435/26; 435/25; 435/18; 435/15; 435/24; 435/14; 435/4; 435/242; 435/243; 435/252.5; 435/834; 435/836; 435/839; 435/837; 435/975; 435/838
[58] Field of Search ............... 435/29, 26, 25, 435/18, 15, 4, 24, 14, 242, 243, 252.5, 834, 836, 837, 838, 839, 975

[56] References Cited

U.S. PATENT DOCUMENTS

| | | | |
|---|---|---|---|
| 4,381,343 | 4/1983 | Citri | 435/24 |
| 4,603,108 | 7/1986 | Bascomb | 435/24 |
| 4,774,173 | 9/1988 | Reinhartz | 435/29 |
| 4,808,517 | 2/1989 | Blondin et al. | 435/4 |
| 5,019,411 | 5/1991 | Johnson et al. | 426/52 |
| 5,149,656 | 9/1992 | Bitton | 435/29 |
| 5,260,213 | 11/1993 | Harman et al. | 435/172.2 |

FOREIGN PATENT DOCUMENTS 1010128  4/1983  U.S.S.R. .

OTHER PUBLICATIONS

J. Gen. Microb., Venkatasubramanian et al, vol. 135, pp. 2723–2733, 1989.
Kniest et al (Abstract) Biotechnology Techniques, vol. 4 (4) p. 269, (1990).

*Primary Examiner*—John Kight
*Assistant Examiner*—Louise Leary
*Attorney, Agent, or Firm*—Steinberg, Raskin & Davidson, P.C.

[57] ABSTRACT

The invention provides a method for the rapid detection of biotoxic contaminants in a test material comprising combining a sample of the test material with activated spores essentially devoid of detectable enzymatic activity, which activity becomes manifest and increases measurably following germination of the spores and with at least one germinant capable of triggering germination of the spores and a substrate which is catalytically convertible to a product by the enzymatic activity, incubating the mixture for a period of less than one hour to accelarate germination of the spores, increase of the enzyme activity, and a catalytic conversion of the substrate, and detecting the formation of the product of the catalytic conversion of the substrate and the enzyme, the level of the product being maximal in the absence of any biotoxic contaminants, and decreasing in direct proportion to the toxicity of contaminants in the test sample.

20 Claims, No Drawings

METHOD AND TEST KIT FOR THE RAPID DETECTION OF BIOTOXIC CONTAMINANTS

The present invention relates to a method and test kit for the rapid detection of biotoxic contaminants.

A test system for biotoxicity can be defined as a biological detector that provides information about the toxicity of a sample to living organisms. There are several good test systems available, but there is no single text system that can detect all biotoxic components with adequate sensitivity.

Heretofor the approach has been to use batteries of tests so as to ensure a broader range of sensitivity. The most common application of such test batteries is the testing of sediments, effluents, leachates and muds. For obvious reasons there is now a tendency to replace animal test organisms with plant seeds, algae and microorganisms in constructing miniaturized test batteries.

The following table summarizes data regarding four currently used miniaturized test systems.

TABLE 1

SUMMARY OF FOUR MINIATURIZED BIOASSAYS

| Organism | Measurement | Source of organism | Exposure/ Technical Time | Sample Volume |
|---|---|---|---|---|
| Selenastrum | 14C uptake via fresh water green algae | laboratory culture | 24/2 hr. | 5 ml |
| Microtox | luminescence in marine bacteria | freeze dried culture commercially available | 15 mins/ 1 hr | 3 ml |
| Brachionus calyciflorus | survival of freshwater rotifer | cultured from cysts. | 24/1 hr | 5 ml |
| lettuce | root elongation of lettuce seeds | commercially available seeds | 96/3 hr | 23 ml |

While all such systems are more flexible and economical than animal tests, the only kit that provides results within one hour, rather than after a day or more, is the Microtox kit, which is based on the luminescence of marine bacteria. However, the choice of such bacteria suffers from two basic disadvantages. First, the marine origin of the test organism dictates the use of test media resembling the marine habitat and thus is often incompatible with the nature of the test sample. Second, the viability of the luminescent bacterial preparations cannot be preserved except under very demanding terms of handling and storage. This increases the costs of the system by a large factor and imposes severe limitations on the range of conditions, e.g. in the field, where immediate reliable testing is often an important advantage.

The present invention offers a singular solution to both of the above problems, which are inherent in the test system. The test organism in the present system is the bacterial spore formed by any of the aerobic bacterial strains normally found in soil, fresh water or dust. This solves the problem of habitat and that of stability since bacterial spores are known to represent the most resistant forms of life. The unparalleled resistance allows the spores to survive under virtually any conditions and thus provides an ideal reagent for field use. However, because of their resistance to noxious agents, spores as such cannot be used for sensing biotoxicity. The sensing is done by the germinating spores which is one of the most actively developing and responsive forms of life. According to the present invention, biotoxic contaminants will be detected through their interference with functions subsequent to germination and, specifically, with the synthesis of enzymes accompanying outgrowth and consequent vegetative cell formation. The appearance of activity of an enzyme following germination in the presence of a test sample will provide a clear and readily quantifiable indicator of the effect of that sample on a living system.

Furthermore, according to the present invention the employment of germinating bacterial spores originating in soil, water, dust and similar relevant environments implies that a variety of spores, differing in their respective sensitivities to polluting biotoxicants, can be combined as desired to construct a greatly improved miniature test battery.

Thus, according to the present invention there is now provided a method for the rapid detection of biotoxic contaminants in a test material comprising:

a) combining a sample of said test material with activated spores essentially devoid of detectable enzymatic activity, which activity becomes manifest and increases measurably following germination of said spores and with at least one germinant capable of triggering germination of said spores and a substrate which is catalytically convertible to a product by said enzymatic activity;

b) incubating said mixture for a period of less than one hour to accelarate germination of said spores, increase of said enzyme activity, and a catalytic conversion of said substrate; and c) detecting the formation of the product of the catalytic conversion of said substrate and said enzyme, the level of said product being maximal in the absence of any biotoxic contaminants, and decreasing in direct proportion to the toxicity of contaminants in said test sample.

In preferred embodiments of the present invention, the said incubation is carried out for a period of less than 30 minutes.

The invention also provides a test kit for carrying out the above method, comprising a swab impregnated with dry spores essentially devoid of detectable enzymatic activity, which activity becomes manifest and increases measurably following germination of said spores, as well as providing a test kit further comprising a test tube provided with a dry reaction mixture containing at least one germinant capable of triggering germination of said spores and a substrate which is catalytically convertible to a product by said enzymatic activity and a test kit, further comprising an assay surface impregnated with an assay reagent for detecting the product of the catalytic conversion of said substrate and said enzyme.

In this embodiment said swab serves both as the carrier of the spores and as the sampling device.

In another embodiment of the present invention there is provided a test kit for carrying out the above-identified method, comprising a) activated dry spores essentially devoid of detectable enzymatic activity, which activity becomes manifest and increases measurably following germination of said spores; and b) a dry reagent mixture containing at least one germinant capable of triggering germination of said spores and a substrate which is catalytically convertible to a product by said enzymatic activity.

The advantages of the presently described test method and kit can be summarized as follows:

1. Stability: the bacterial spore is the most stable form of life.
2. Rapidity: the spores can be activated [e.g. by heating to 60° C. for 30 mins] so as to respond within minutes to a germinant and to respond, consequently and without delay, to the presence of biotoxic pollutants.
3. Flexibility: there is a fair variety of enzymes that can be shown to be appropriate indicators of outgrowth following germination; hence deficiency in each such enzyme testifies to the presence of a noxious factor in the test sample. The ability to choose from an array of available enzymes is a unique advantage of the present invention.
4. Sensitivity: enzyme activity is accepted as a most sensitive and a most precisely quanifiable parameter and as such it tends to replace other indicators wherever possible.

Several spore formers and suitable germinants for use in the present invention are listed hereinafter in Table 2.

TABLE 2

EXAMPLES OF SPOREFORMERS AND GERMINANTS

| Spore forming bacteria | Natural Habitat | Germination trigger (germinant) |
|---|---|---|
| Bacillus licheniformis | Soil, dust, water | Inosine; glucose |
| Bacillus subtilis | Soil, water, hay | L-alanine |
| Bacillus cereus | Soil | L-alanine; adenosine |
| Bacillus megaterium | Dust, soil, water | KBr; L-proline; glucose |
| Bacillus polymyxa | Soil, sewage | L-alanine |

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Photometric determination of biotoxicity with spores of Bacillus licheniformis

The test sample consists of 1.0 ml of lake water and an equal volume [1.0 ml] of triple distilled sterile water is used as a pure control. The sample and the control are each placed in separate test tubes each containing a dry mixture consisting of benzylpenicillin [6 mg], L-alanine [5 µg] and glucose [20 mg]. After adding to each tube 0.2 ml of phosphate buffer [pH7.6; 0.04M] prepared in 0.008% phenol red and containing activated spores [OD 0.6] of Bacillus licheniformis [strain 749/c] both test tubes are incubated [30 min at 30° C.]. The change of color in the test sample is compared with that in the control with the aid of a photometer, preferably at 558 mu. A calibration curve is used to correlate reduced decrease in optical density, relative to control, with the level of biotoxicity of the lake water contaminant.

EXAMPLE 2

Iodometric evaluation of biotoxicity in water.

In this assay activity of germinating spores is inversely proportional to the time required for decolorization of a standard amount of iodine by the product of the penicillinase formed following germination. Activated spores of Bacillus cereus [strain 569] were used in the experiment described below:

Reaction mixture [total volume—0.25 ml]:
  Adenosine—0.1 mM; L-Alanin—0.1 mM; gelatin—0.5% phenoxymethhylpenicillin—1.5 mg; Spores—100 million CFU; Phosphate buffer [pH 7.2; 0.1M]

Test samples consisted of fresh spring water spiked with mercuric chloride as indicated in Table 1. Each sample [0.025 ml] was incubated [40 min at 37° C.] in a test tube containing 0.25 ml of the reaction mixture of the above composition.

Assay of activity:

The incubation was terminated by the addition of 0.2 mL of an assay reagent composed of 50 mM potassium iodide and 10 mM iodine in a 0.75% aquous starch solution. The decolorization time of each sample was recorded [see Table 3.

TABLE 3

| Sample # | Mercuric Chloride [mM] | Decolorization time [seconds] | |
|---|---|---|---|
| | | Expt #1 | Expt #2 |
| 1 | 0 | 75 | 70 |
| 2 | 0.005 | 90 | 92 |
| 3 | 0.010 | 95 | 95 |
| 4 | 0.020 | 145 | 150 |
| 5 | 0.030 | 480 | 540 |
| 6 | 0.050 | 900 | 840 |
| 7 | 0.100 | 1100 | 1200 |

A plot of reciprocal values of the decolorization times against the concentrations of mercuric chloride yielded the value of EC=0.017 mM for mercuric chloride.

EXAMPLE 3

Detection of biotoxic agents in mud.

The following method is based on the same principle as that described in Example 2, but it is specially adapted for use with samples that are non-transparent or otherwise interfere with optical determination. The composition of the reaction mixture is as in Example 2. However, the spores, in this embodiment, are preferably not introduced directly into the reaction mixture in the form of a spore suspension. Instead, the spore suspension is used to impregnate the tip of a cotton-wool swab. After drying such swabs can be maintained indefinitely at ambient temperatures and used as needed for sampling mud, sediments, extracts as well as any liquids—by the simple procedure of dipping said swab in the test sample. Thereafter the swab is placed in the reaction mixture and incubated for 30 min at 37° C. The swab is then used to wet a selected spot on a strip or card of paper impregnated with the assay reagent described in Example 2. Such reagent papers can be stored indefinitely after drying if protected from light, moisture and excessive heat. The wet spot will decolorize if penicillinase was formed in the presence of the test sample. This test is not strictly quantitative, but a semi-quantitative assay can be run if positive controls are included in the test procedure.

A permanent record of the results can be retained when the test is completed and the assay paper dried and stored as recommended above.

EXAMPLE 4

Detection of biotoxic levels of a surfactant in effluent samples

In this example the spores are derived from Bacillus subtilis ATCC 6633 and the germination signal is a change in the redox potential as reflected in a color change observed visually in Resazurin, a redox indicator incorporated in the reaction mixture which may be otherwise similar to that in Example 2. The redox shift is of course caused by a chain of oxidoreductive events catalysed by enzymes that have been dormant or absent before germination.

The spores of B. subtilis can be replaced with many other bacterial spores, and several other redox indicator dyes [e.g. methylene blue, various tetrazolium salts] may be used for visual detection or photometric determination of activity subsequent to germination and for estimating or measuring, respectively, the levels of biotoxic pollutants that interfere with the normal physiology of the germinating spore.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for the rapid detection of biotoxic contaminants in a test material comprising:
   a) forming a mixture by combining a sample of said test material with
      (i) activated spores essentially devoid of detactable enzymetic activity,
      (ii) a germinant capable of triggering germination of said spores, and
      (iii) a substrate,
      said activated spore enzymatic activity becoming manifest and increasingly measurably following germination of said spores with said germinant and said substrate capable of being catalytically convertible into a product by said enzymatic activity;
   b) incubating said mixture for a period of less than one hour to accelerate germination of said spores, and to increase said enzymatic activity, and catalytic conversion of said substrate to said product; and
   c) detecting the level of said product formed, the level of said product being maximal in the absence of any biotoxic contaminants, and decreasing in direct proportion to the toxicity of contaminants in said test sample.

2. The method of claim 1, wherein said incubating is carried out for a period of less than 30 minutes.

3. A method for the rapid detection of biotoxic contaminants in a test material comprising:
   (a) forming a mixture by combining a sample of said test material with
      (i) activated spores essentially devoid of detectable enzymatic activity,
      (ii) a germinant capable of triggering germination of said spores, and
      (iii) a substrate,
      said activated spore enzymatic activity becoming manifest and increasing measurably following germination of said spores with said germinant anti said substrate is catalytically convertible into a product by said enzymatic activity;
   b) incubating said mixture for a period of less than one hour to accelerate termination of said spores, and to increase said enzymatic activity, and catalytic conversion of said substrate to said product; and
   c) determining the level of biotoxic contaminants by detecting the level of said product formed, the level of said product being maximal in the absence of any biotoxic contaminants, and decreasing in direct proportion to be toxicity of contaminants in said test sample.

4. The method of claim 3, wherein said spores are selected from the group consisting of *Bacillus linchenformis, Bacillus subtilis, Bacillus cereus, Bacillus megaterium*, and *Bacillus polymya spores*.

5. The method of claim 3 wherein said germinant is selected from the group consisting of inosine, glucose, L-alanine, adenosine, L-proline and KBr.

6. The method of claim 4, wherein said spores are *Bacillus lichenformis* spores and said germinant is selected from the group consisting of inosine and glucose.

7. The method of claim 4, wherein said spores are *Bacillus subtilis* spores and said germinant is L-alanine.

8. The method of claim 4, wherein said spores are of *Bacillus cereus* and said germinant is selected from the group consisting of L-alanine and adenosine.

9. The method of claim 4, wherein said spores are *Bacillus megaterium* spores and said germinant is selected from the group consisting of KBr, L-proline and adenosine.

10. The method of claim 4, wherein said spores are *Bacillus polymya* spores and said germinant is L-alanine.

11. The method of claim 3, wherein germination is detected by a change in redox potential produced by a redox indicator incorporated in said mixture.

12. The method of claim 11 wherein the redox indicator is a tetrazoline compound or a salt thereof.

13. A test kit for carrying out the method of claim 3 comprising a swab impregnated with dry spores essentially devoid of detectable enzymatic activity, which activity becomes manifest and increases measurably following germination of said spores.

14. The test kit of claim 13 further comprising a test tube provided with a dry reaction mixture containing at least one germinant capable of triggering germination of said spores and a substrate which is catalytically convertible to a product by said enzymatic activity.

15. The test kit of claim 13 further comprising an assay surface impregnated with an assay reagent for detecting the product of the catalytic conversion of said substrate and said enzyme.

16. A test kit for carrying the method of claim 3, comprising spores essentially devoid of detectable enzymatic activity, which activity becomes manifest and increases measurably following germination of said spores, and with at least one germinant capable of triggering germination of said spores and a substrate which is catalytically convertible to a product by said enzymatic activity.

17. The test kit of claim 13 wherein said spores are selected from the group consisting of *Bacillus linchenfonnis, Bacillus subtilis, Bacillus cereus, Bacillus megaterium*, and *Bacillus polymya*.

18. The test kit of claim 14 wherein said germinant is selected from the group consisting of inosine, glucose, L-alanine, adenosine, L-proline and KBr.

19. The test kit of claim 13 wherein said assay reagent is a redox indicator.

20. The test kit of claim 13 wherein said assay reagent is methylene blue.

* * * * *